(12) United States Patent
Case et al.

(10) Patent No.: US 9,895,227 B2
(45) Date of Patent: Feb. 20, 2018

(54) PROSTHESIS ADAPTED FOR PLACEMENT UNDER EXTERNAL IMAGING

(75) Inventors: Brian C. Case, Bloomington, IN (US); Jacob A. Flagle, Bloomington, IN (US); Michael L. Garrison, Indianapolis, IN (US); Andrew K. Hoffa, Bloomington, IN (US); Ray Leonard, II, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1269 days.

(21) Appl. No.: 13/444,238

(22) Filed: Apr. 11, 2012

(65) Prior Publication Data

US 2012/0253450 A1   Oct. 4, 2012

Related U.S. Application Data

(62) Division of application No. 10/787,307, filed on Feb. 26, 2004, now Pat. No. 8,157,810.

(60) Provisional application No. 60/450,396, filed on Feb. 26, 2003.

(51) Int. Cl.
*A61F 2/82* (2013.01)
*A61F 2/24* (2006.01)
*A61B 90/00* (2016.01)

(52) U.S. Cl.
CPC .......... *A61F 2/2475* (2013.01); *A61B 90/39* (2016.02); *A61F 2/2418* (2013.01); *A61F 2230/0026* (2013.01); *A61F 2230/0095* (2013.01); *A61F 2250/0098* (2013.01)

(58) Field of Classification Search
CPC ........................................................ A61F 2/82
USPC ................................. 623/1.34, 1.24
See application file for complete search history.

(56) References Cited

U.S. PATENT DOCUMENTS

| | | | |
|---|---|---|---|
| 6,010,531 A | 1/2000 | Donlon et al. | |
| 6,074,419 A | 6/2000 | Healy et al. | |
| 6,299,604 B1 | 10/2001 | Ragheb et al. | |
| 6,334,871 B1* | 1/2002 | Dor et al. | ..... 623/1.34 |
| 6,508,824 B1 | 1/2003 | Flaherty et al. | |
| 6,602,241 B2 | 8/2003 | Makower et al. | |
| 7,179,270 B2 | 2/2007 | Makower | |
| 7,491,942 B2 | 2/2009 | Black et al. | |
| 7,653,455 B2 | 1/2010 | Cinader, Jr. | |
| 8,157,810 B2 | 4/2012 | Case et al. | |

(Continued)

*Primary Examiner* — Matthew Schall
(74) *Attorney, Agent, or Firm* — Buchanan Van Tuinen LLC (57) ABSTRACT

An expandable prosthesis having an imageable structure comprising one or more elements visually distinguishable by an external (e.g., radiographic or ultrasonic) imaging system, the structure being located about a first axis that corresponds to a structural feature of the prosthesis that is configured to perform a specific function particular to that axis. The imageable structure is configured to assist in the rotational orientation of the prosthesis during placement within the implantation site. In one embodiment, the prosthesis comprises a venous valve that includes imageable elements or structure, such as a pair of radiopaque markers, that defines the orifice of the valve structure such that the orifice can be oriented with a particular anatomical feature under imaging, such as to align the orifice with the long axis of the vessel.

2 Claims, 8 Drawing Sheets

(56) References Cited

U.S. PATENT DOCUMENTS

| | | |
|---|---|---|
| 2001/0007956 A1 | 7/2001 | Letac et al. |
| 2001/0021872 A1 | 9/2001 | Bailey et al. |
| 2002/0032414 A1 | 3/2002 | Ragheb et al. |
| 2003/0023303 A1 | 1/2003 | Palmaz et al. |
| 2003/0036794 A1 | 2/2003 | Ragheb et al. |
| 2003/0040792 A1 | 2/2003 | Gabbay |
| 2003/0149477 A1 | 8/2003 | Gabbay |
| 2003/0181973 A1 | 9/2003 | Sahota |
| 2004/0006380 A1 | 1/2004 | Buck et al. |
| 2005/0113686 A1 | 5/2005 | Peckham et al. |
| 2008/0125860 A1 | 5/2008 | Webler et al. |

\* cited by examiner

PROSTHESIS ADAPTED FOR PLACEMENT UNDER EXTERNAL IMAGING

TECHNICAL FIELD

This invention relates to medical devices, more particularly to intraluminal prosthesis, such as valves, stents, and the like, placed using external imaging methods.

BACKGROUND OF THE INVENTION

Prosthetic or artificial valves have been developed for placement in the venous system to augment or replace native valves whose functionality has been compromised. Valves become incompetent when the cusps cannot close sufficiently to prevent reflux of blood, thereby causing it to pool in the lower extremities which often leads to painful swelling of the lower legs and feet.

Based on the initial animal and clinical experience with the placement of prosthetic venous valves to treat chronic venous insufficiency in the lower extremities, some physicians feel that placement strategies play an important role in the efficacy of the treatment. One strategy is to place the prosthetic valve near or across the native valve to take advantage of what functionality may still exist and/or derive the optimal physiological location. The deep veins of the legs typically have a elliptical cross-sectional shape due to compression by the adjacent muscles that lie on either side of the vessel. It is the action of these muscles against the vessel that help to propel the blood toward the heart. During investigational animal studies of our own early prototype venous valves, efforts were under to orient the orifice with the long axis of the vessel in the expectation that such an orientation would improve functionality of the valve. This proved difficult to accomplish under fluoroscopy since that the leaflet structure and support structure of a typical artificial valve offers little or no visual guidance to aid in aligning the orifice accordingly. While gold or other radiopaque markers have been used to identify the ends of coronary and other types of stents to aid in longitudinal positioning across a stricture, lesion, or other target site (e.g., U.S. Pat. No. 6,409,752), the need for circumferential orientation has generally not been addressed and thus, previous marker arrangements have not been designed to be particularly useful for that purpose. Needless to say, if a specific orientation of the prosthesis is critical, it must be accomplished prior to deployment, particularly if the prosthesis is self-fixating, such as by virtue of barbs or other anchoring structure.

What is needed is a prosthesis having a preferred circumferential orientation within the vessel that includes structure or some means by which the clinician can readily ascertain under fluoroscopy or some other imaging system, whether the prosthesis is correctly rotated within the vessel prior to deployment.

SUMMARY OF THE INVENTION

The foregoing problems are solved and a technical advance is achieved in an illustrative prosthesis placeable into a body lumen and which comprises a support structure configured to engage the walls of the body lumen, the prosthesis having a cross-sectional profile that includes a first axis traversing at least one structural feature or characteristic of the prosthesis adapted and configured to provide a specialized function particular to the first axis or a location therealong, that function be separate from that of the remainder of the support structure, which typically is to engage the walls of the bodily, anchor the prosthesis, and/or maintain a patent passageway. The first axis transects the passageway of the prosthesis support structure with structural feature lying either across the axis or at one or more point along the axis, such as along the periphery of the prosthesis. The prosthesis further includes one or more imageable element, such as radiopaque markers, located about the first axis that are configured to allow one to identify the orientation of the first axis relative to an anatomical feature of the body lumen while the prosthesis is being placed using external imaging guidance. For purposes of this application, terms >radiopaque markers= and >radiopaque material= are understood to mean any element or structure comprising or consisting of a high-density material (e.g., gold, platinum, tantalum, tungsten, barium, bismuth, etc.) in a sufficient quantity that the marker is readily visible and distinguishable from adjacent structure under radiographic (fluoroscopic or x-ray) imaging.

In one aspect of the invention, the prosthesis comprises an artificial valve that opens and closes in response to fluid flowing therethrough and changes in the pressure differentials on either side of the valve. The artificial valve includes a plurality of leaflets, such as a pair of opposing leaflets, that define an orifice therethrough. In one embodiment, the two imageable elements comprise a first radiopaque member located about the first end of the orifice and a second radiopaque member located about the second end of the orifice (i.e., the outer edges of leaflets defining the orifice) such that under external fluoroscopic imaging, the operator can determine the orientation of the valve within the vessel. The radiopaque markers allow rotational positioning to align the valve with a feature of the vessel, such as at the long axis thereof or the native valve lying adjacent to where the valve is placed. The radiopaque markers can comprise beads of gold or some other radiopaque material that are inserted into the coiled bends and secured by flattening and enlarging the ends so that the bead cannot fall out and/or by securing the bead within a fold of the covering material that is sutured or otherwise attached to the framework of the prosthesis.

In another aspect of the invention, the radiopaque markers are attached to a strut of the framework at strategic locations, such as for permitting identification of the valve orifice. Embodiments include, but are not limited to, pressing or securing a radiopaque metal bead into an aperture formed in the framework (such as one formed when a frame is laser cut from a metal tube); wrapping radiopaque metal wire around the struts; attaching and/or crimping radiopaque metal cannulae over the struts; and applying an outer layer of radiopaque material to the framework, such as by dipping the struts in molten gold or coating with a polymer loaded with a radiopaque filler material.

In yet another aspect of the present invention, selected portions of the frame, such as struts, barbs, etc., are made from a radiopaque material. These elements are aligned with a structural feature of the prosthesis, such as the valve orifice, so that the clinician can ascertain the position of the prosthesis under radiographic imaging.

In still yet another aspect of the present invention, the support structure is configured in a manner that permits identification of particular areas that correspond to a feature of particular importance on the prosthesis. Embodiments include altering the shape, length, or number of struts in a particular location along the circumference of the support structure to provide an imageable marker that is visible under fluoroscopic guidance or some other method of imaging.

In still yet another aspect of the present invention, the imageable structure comprises an ultrasonically reflective surface, such as providing a series of indentations in the surface of the support structure that are configured to reflect sound waves and allow for ultrasound imaging of that particular region. As with the radiographically imageable structure, the ultrasonically reflective surface would be located at selected points along the prosthesis that correspond with a particular critical feature or structure thereof.

In still yet another aspect of the present invention, the imageable structure comprises radiopaque elements that are positioned around an aperture formed through the material that covers a prosthesis, such as a stent graft, so that under radiographic guidance, the aperture can be aligned with a structure such as the opening to a branch vessel or duct.

In still yet another aspect of the invention, imageable markers are placed in strategic locations for allowing the clinician to determine if the prosthesis has been deployed correctly or is otherwise functioning properly. One embodiment includes placing radiopaque markers at selected locations that would indicate if the prosthesis becomes tilted at or following deployment. In another embodiment, the leaflets of a prosthetic valve can include radiopaque or imageable markers or materials that would allow the clinician to determine whether the valve leaflets are opening and closing to effectively regulate blood flow therethrough.

In still another aspect of the invention, imageable markers are used to ensure that the orientation of the orifice of a valve or other structure feature whose longitudinal orientation (proximal or distal within the vessel or bodily lumen) is critical for the function of that particular device. Radiopaque markers or other imageable structure placed about the prosthesis for rotational alignment of the prosthesis may also be adapted for use in proper loading and orientation of the prosthesis within the delivery apparatus. This is of particular importance in a valve prosthesis in which the location and orientation of the valve orifice is important in the functionality of the valve after deployment. Typically, the leaf structure of a vascular valve is configured to allow unidirectional flow such that retrograde flow will cause the valve to close. Thus, if the valve is placed backwards or upside down within the vessel, it becomes an occluder device and in the venous system, rather than a valve, will not permit normal antegrade blood flow back to the heart. As such, it is especially critical that when loading a venous valve into a delivery apparatus, that verification of the correct longitudinal orientation of orifice occurs before the device is used clinically. This can be done by examining the device (delivery apparatus and loaded valve) under fluoroscopy or other appropriate imaging system before the product leaves the manufacturer or at least before it is used within the patient, to ascertain that the radiopaque marker or other imageable structure is oriented correctly to ensure correct function of the valve after deployment.

Radiographic verification is not only important to prevent errors during the loading process, but because the longitudinal orientation of the valve within the delivery apparatus is different depending on whether the delivery approach is ascending (with the delivery catheter coming up from below the implantation site, such as via the femoral vein) or descending, (an approach via a vein above the implantation site, such as the jugular or subclavian veins). In a typical venous valve, the orifice or inner edges of the leaf structure is located at the proximal end (toward the head) so that the leaflets slope at least slightly downward and away, thus being configured to catch blood and close the valve. In the illustrative example of the present invention, the orifice is configured and oriented toward the first or a delivery apparatus intended for an ascending approach, the orifice is generally configured and oriented toward the first or proximal end of the prosthesis. One or more radiopaque markers located at the proximal end allow the clinician to determine that the orifice is oriented toward the distal tip of the delivery apparatus and thus, the delivery apparatus is configured for an ascending approach. For a descending approach, the orifice and associated imageable markers are located at the end of the valve furthest from the distal tip of the delivery apparatus such that when the delivery system is oriented downward with the tip toward the implantation site, the valve will be in its proper orientation.

Preferably, the delivery apparatus valve prosthesis, package, labeling, or instructional materials located within the outer package (the latter three comprising the >packaging material=) include some type of specific indicia or warning or other identification that allows one to determine whether the system is intended for an ascending or descending approach. The imageable structure, preferably located about the orifice at one end of the device, provides further providing confirmation of the orientation of the valve within the delivery apparatus. Besides used for rotational orientation, and confirmation of proper longitudinal orientation, the imageable structure can be used for more precisely placing the orifice in the proper located in the vessel longitudinally.

In another embodiment, the valve prosthesis can be loaded just prior to use in a delivery apparatus configured for either an ascending or descending approach, such as by having the valve preloaded in a loading member, such as a cartridge other constraining element, that is insertable into the passageway of the delivery apparatus and which includes separate indicia or instructions for loading orientation depending on whether an ascending or descending approach is to be used. The indicia for facilitating proper orientation and loading of the valve into the delivery apparatus can be imageable, such as a radiopaque marker on the valve or radiopaque marker or band around a particular end of the loading cartridge, or it may include other types of external indicia (lettering, color(s), variable shapes, etc.) that allow one to determine the orientation fo the valve during loading for a particular delivery approach. For purposes of defining the scope of the invention, the loading element is considered part of the prosthesis in determining the presence or location of imageable structure on the prosthesis relative the orifice or other structural feature while the prosthesis (and loading element) is inside the delivery apparatus.

BRIEF DESCRIPTION OF THE DRAWING

Embodiments of the present invention will now be described by way of example with reference to the accompanying drawings, in which.

DETAILED DESCRIPTION

As embodied in FIGS. 1-23, the present invention is exemplified by an intraluminal prosthesis, typically of a generally tubular or cylindrical shape (cylindrical being defined to include flared or variable-diameter configurations), such as a expandable or self-expanding artificial valve 10, stent, stent graft, occluder, shunt, filter, or the like, that further comprises elements or structure that allows a clinician, using a selected means of external guidance, such as fluoroscopy, X-ray, ultrasound, M.R.I., etc., to readily identify the plane in which the prosthesis, or a particular portion thereof, lies prior to deployment within the patient and/or immediately thereafter. For example, to identify a structural feature 24,82, etc., disposed about a first axis 97 transecting the passageway 96 of the prosthesis, the imageable structure the imageable structure 12 or element is configured or positioned about the axis 97 to allow the clinician to adjust the position of the prosthesis (e.g., by rotation) within the bodily lumen such that the structural feature of the prosthesis, such as an orifice 24, aperture, port, specialized anchoring element (whose orientation is particularly critical), covering, leaflet, or other difficult-to-discern structure that has a separate function that the general support structure. The external imaging guidance system allows the clinician to orient or locate the structure feature relative to the support structure. By ascertaining the rotational orientation of the first axis 97, the structural feature can be aligned to a particular orientation or feature of the patient=s anatomy so that the prosthesis will function in a desired or preferred manner. Examples of a particular feature of the patient=s anatomy to which the orientation of a prosthesis could be manipulated would include the shape of a vessel or duct, such as its cross-sectional shape (e.g., elliptical), a particular bend or contour; a branch or shunt of a vessel or duct; a valve, sphincter, organ, gland, or other native structure; a stenosis or stricture, or any other anatomical feature that would affect how the prosthesis is placed within the vessel or duct. For definition purposes, the prosthesis of the present invention comprises a general structure or configuration that would not ordinarily include imageable features related to its primary function that would otherwise allow reliable identification of its orientation under external imaging without the incorporation of the supplemental imageable structure or elements of the present invention that correspond to a functional characteristic of the device. It is acknowledged that most prosthetic devices include a frame or structure that is at least somewhat visible under at least one external imaging method, such as fluoroscopy, ultrasonograhpy, etc. However, only a subset of these prosthetic devices includes a structural adaptation for enhancing the ability of the device to be placed using external imaging, and typically such structural elements are limited to those, such as radiopaque markers at one or more ends of the device for facilitating placement at a target location, and do not correspond with a structural adaption of the device for performing any particular function. The scope that includes prostheses having a specific orientation corresponding to an anatomical feature of the patent (but lacking useful inherent structural features that are imageable) would specifically exclude prosthetic devices that are bifurcated (such as a stent graft for excluding aneurysms), have imageable side branches, or comprise a specific imageable shape is associated with the primary function of the device and that also permits ready identification of rotational or other orientation without requiring supplemental imageable structure adapted for providing such identification. Examples of prosthetic devices included in the scope of the invention include, coronary and other basic tubular stents or stent grafts, artificial valves, occlusive devices, shunts, and other prostheses whose support structure lacks a distinctive profile to allow identification of whether the prosthesis has attained the critical or desired orientation or position within the patient.

Figure 1:
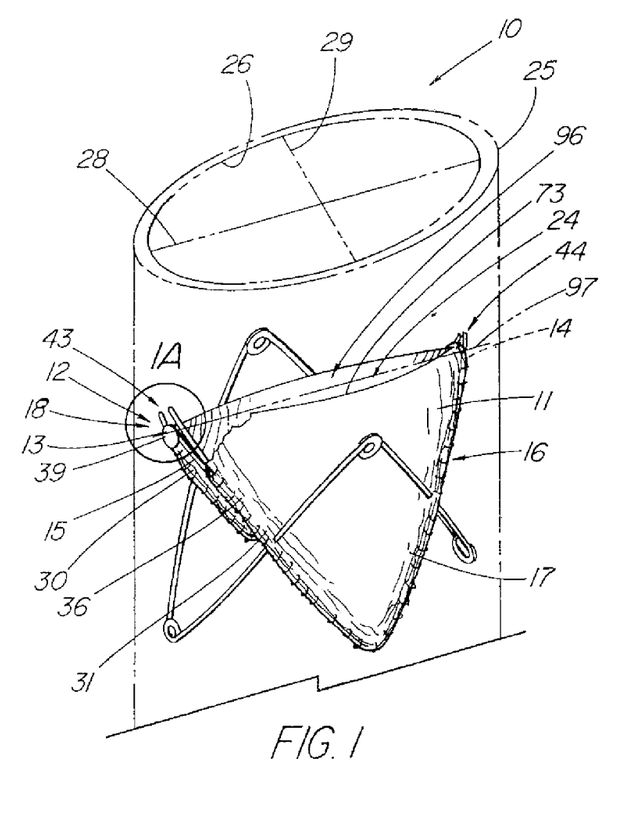
FIG. 1 depicts a perspective view of an artificial venous valve of the present invention.
Figure 1A:
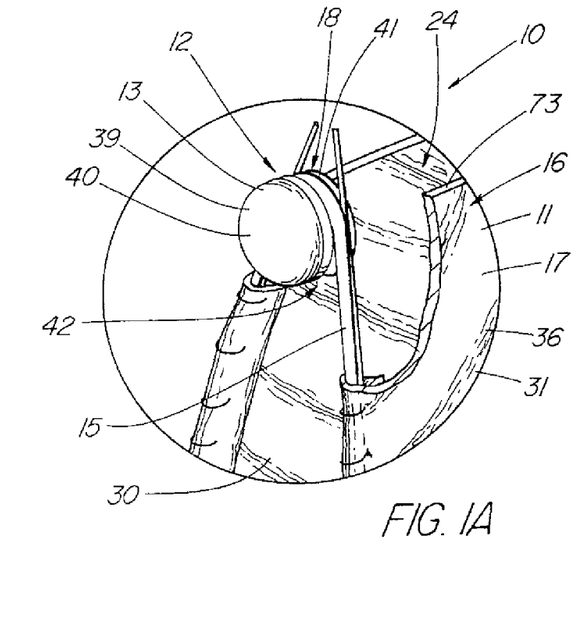
FIG. 1A depicts a detailed view taken from FIG. 1.
Figure 10:
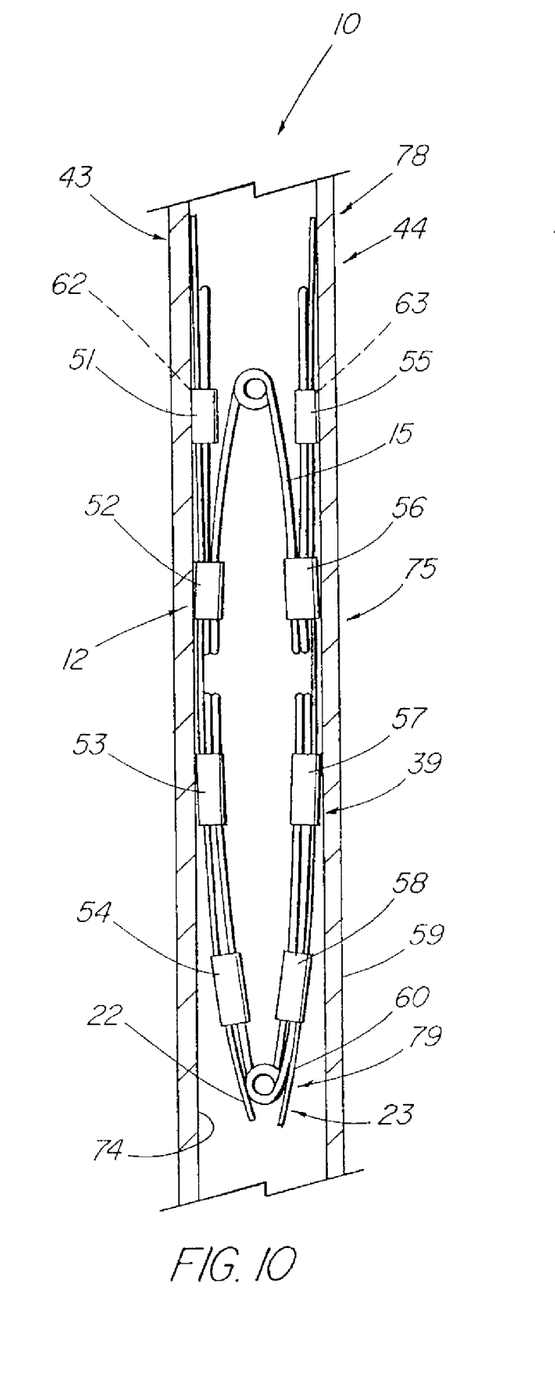
FIG. 10 depicts a partially sectioned view of the support structure of FIG. 9 compressed within a delivery catheter.

FIGS. 1-1a depict a first embodiment of the present invention comprising a prosthetic valve 11, such as the illustrative artificial venous valve used to augment or replace the function of a patient=s incompetent native valve, typically located within the deep veins of the legs, whose function has been compromised due to disease or age-related factors. The illustrative valve 11 includes a leaf structure 16, such as a covering 36 comprising a pair of leaflets 17 attached to a first and second leg 30,31 that comprise a portion of the support structure 15 or frame of the prosthesis 10. The illustrative leaflets 17 are attached to struts of the frame 15 by folding the covering 36 over itself and the frame and securing it with a series of sutures or some other suitable method, such as adhesives, laser tissue welding, etc. The imageable structure 12 of the present invention comprises a first and a second imageable element or marker 13,14, such as the illustrative gold radiopaque members 39, which are located about each end of the elongate orifice 24 of the valve (the first and second ends of the orifice being generally coincident with bends 43 and 44 in the illustrative example), the orifice being defined by either a slit formed within the leaf structure 16 or the opening adjacent to and between the inner edges 73 of the opposing leaflets 17. The arrangement of the two markers 13,14 allows the physician, under fluoroscopic guidance, to determine the orientation of the orifice by the location of the markers 13,14 relative to one another as they appear on the viewing monitor. In the exemplary blood vessel 25, there is a long axis 28 of the cross-sectional vein, lying generally parallel with the muscles compressing the outer walls thereof (not pictured), and a short axis 29 perpendicular to the long axis. Typically, but not always, the cusps of the native valve, are oriented such that the natural orifice lies along the long axis 97. Thus, if the prosthetic valve 11 is to be placed to align the leaflets 17 and orifice 24 with the native valve cusps (not pictured), the radiologist or clinician can rely on the radiopaque members 39 comprising the first and second markers 13,14 to determine if the prosthetic valve orifice is aligned with the long axis 28 of the vessel (assuming the viewing angle is perpendicular to the long axis 28). This would be the case if the markers 13,14 appear at the right and left edges of opposite inner walls 26 of the vessel 25 and have the maximum available spacing therebetween. Conversely, if the markers 13, 14 are generally superimposed over one another within the same viewing angle, it would indicate that the general alignment is with the short axis 29. By rotating the delivery catheter or system prior to deployment, the physician can correctly align the prosthetic valve 11 with the long axis 28. Preferably, this is performed while the prosthesis 10 is in the compressed state 75, such as depicted in FIG. 10, which shows the support structure 15 (lacking a leaf structure) compressed within a delivery member 59, such as an introducer catheter. While the purpose of FIG. 10 is to illustrate a variety of embodiments of imageable structure of the present invention, it can serve to illustrate how a prosthetic valve would appear under fluoroscopic imaging when the orifice 24 (FIG. 1) is perpendicular to the viewing angle, assuming that bends 43 and 44 represent the respective imageable radiopaque markers (not actually shown), such that they appear as two distinct members located along the inner walls 74 of the delivery member 59. If the prosthesis 10 were to be rotated 90⌐, the radiopaque marker would appear as a single point located midway within the delivery member 59. Thus, as long as the plane of the long axis 28 of the vessel is known, the prosthesis 10 can be aligned using the imageable structure 12 for orientation.

Figure 2:
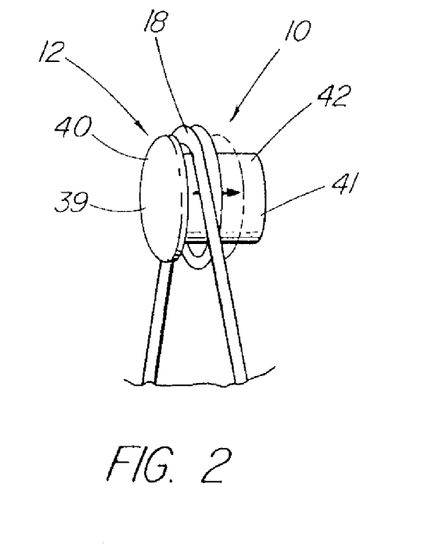
FIGS. 2-4 depict the steps of placing and securing the radiopaque marker of the embodiment of FIG. 1 into a prosthesis having a covering.

FIGS. 1-2 depict a first embodiment of imageable structure 12 comprising a radiopaque member 39, such as a bead comprising gold, platinum, tantalum, tungsten, or some other radiopaque material, that is inserted and secured within a coiled bend 18 of the support structure. The illustrative radiopaque member 39 includes an intermediate or central portion 42 having an outer diameter that is less than the inner diameter of the coiled bend 18, such that there is sufficient room or >play= that the radiopaque member 39 does not interfere with the function of the coiled bend 18 when flexing occurs. The first end portion 40 comprises a larger diameter than the inner coil 18 diameter to help maintain the radiopaque marker 39 in place. FIG. 2 depicts a method of securing the radiopaque marker 39 in which the second end portion 41 is formed smaller than the inner coil 18 diameter so that it may be inserted through the coiled bend 18. Afterward, force is applied against the second end portion 41 using a suitable instrument or means to deform the metal of the second end 41 and increase its diameter (FIG. 1*a*) such that the radiopaque member 39 is secure at both ends and cannot fall out of the passageway defined by the coiled bend 18.

Figure 3:
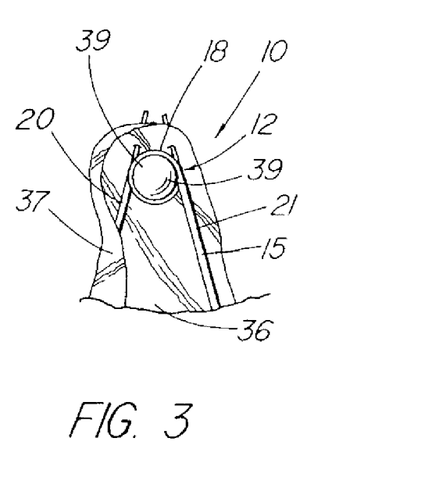
Figure 4:
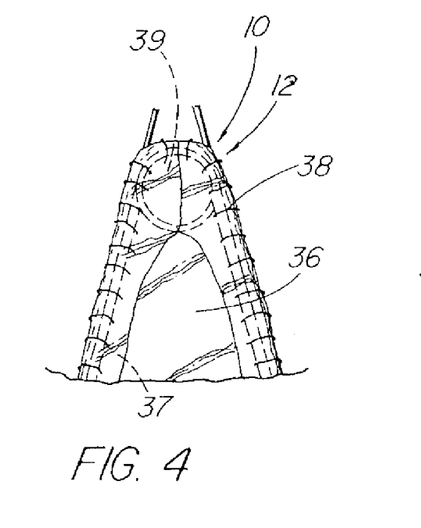
Figure 5:
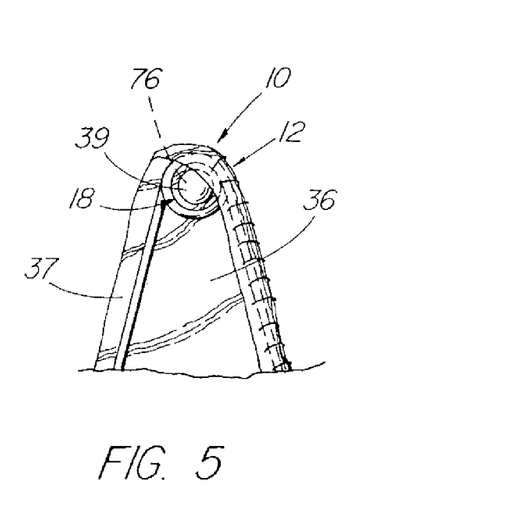
FIG. 5 depicts the placement of an embodiment of radiopaque marker into a prosthesis of the present invention having a covering.

Additional prevention against the radiopaque member 39 becoming separated from the support structure 15 can be attained by enclosing or sealing the coiled bend 18 and radiopaque member 39 together, such as the method depicted in FIGS. 3-4. The excess or overhang 37 of the covering 36 made of a biomaterial (such as small intestinal submucosa or another extracellular collagen matrix) or woven material comprising the leaflet 17 is folded over the bend 18 and adjacent struts 20,21 of the support structure 15 (FIG. 3) and secured with sutures 38 or some other method of sealing or joining the covering 36 (FIG. 4), thereby completely enclosing the radiopaque member 39 in a pocket. As depicted in FIG. 5, the same method can be used to enclose a spherical bead 76 or other radiopaque element 39 which lacks a specific structural modification, such as the enlarged end portions 40,41 of FIG. 1A, to hold the bead within the coiled bend 18 unless sealed therein by another means. Alternatively, the bead or radiopaque marker 39 can be inserted under the fold 37 (overhang) of the fabric at a location outside of the bend and secured therein.

Figures 6, 7, 8, 9:
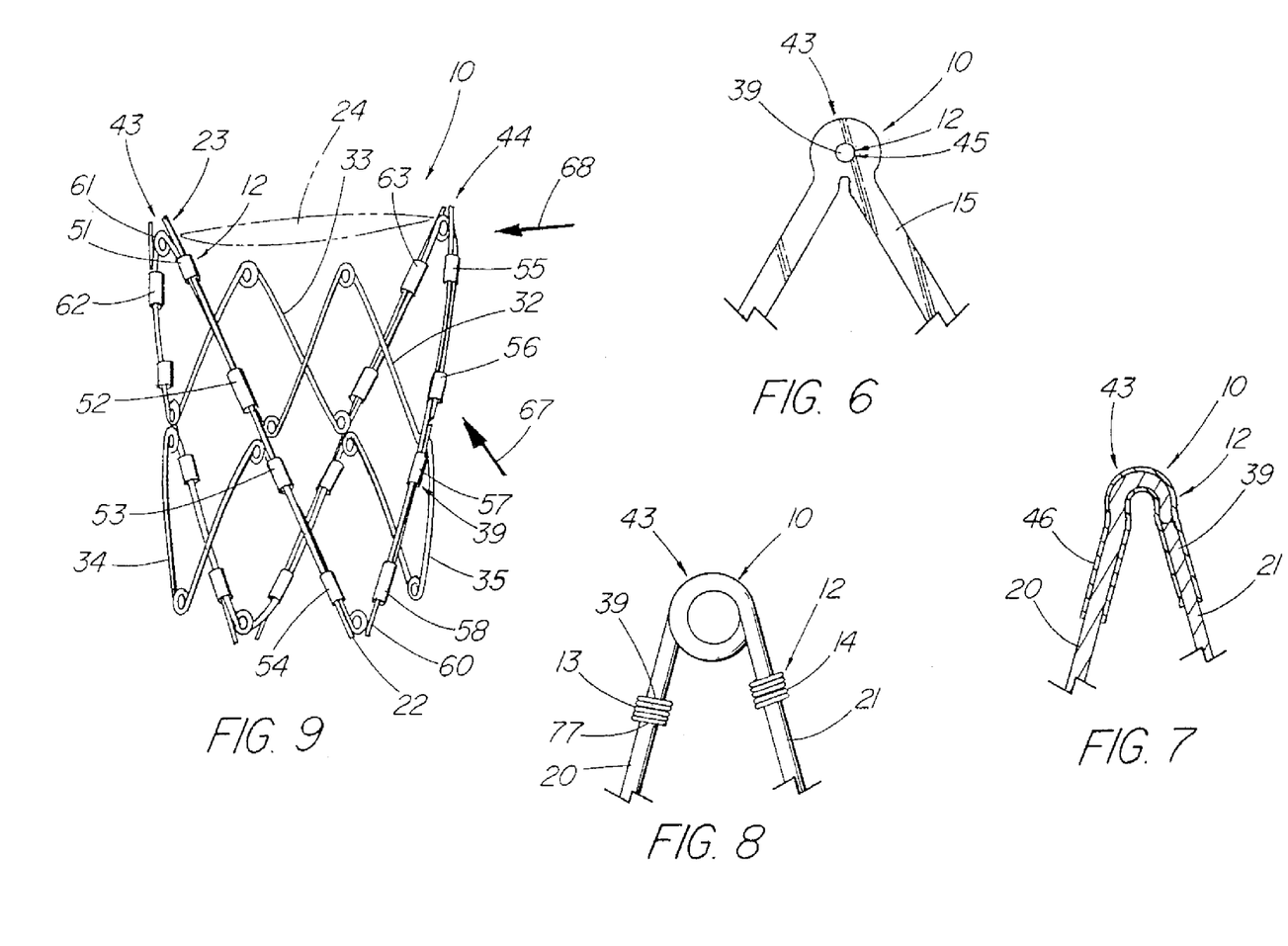
FIG. 6 depicts a side view of an embodiment of an illustrative radiopaque marker that is embedded within the support structure.
FIG. 7 depicts a side view of an embodiment of an illustrative imageable structure that comprises a thick layer of radiopaque material.
FIG. 8 depicts a side view of an embodiment of an illustrative radiopaque marker comprising thin radiopaque wire wrapped around the support structure.
FIG. 9 depicts a perspective view of the support structure of the embodiment of FIG. 1.

Alternative embodiments of radiopaque members 39 or structure may be better adapted for use in a particular type of intraluminal prostheses, especially those lacking coiled bends. FIG. 6 depicts a radiopaque member 39, such as a small gold bead, that has been pressed into an aperture formed within a strut at or near the bend 43 of the support structure 15 of a prosthesis. The radiopaque member 39 is preferably ground down or polished until it is flush with the surface of the support structure. The marker is preferably tapered to help lock the marker within the aperture to prevent it from becoming dislodged. As with the embodiment of FIG. 1, the imbedded radiopaque member 39 can represent one of a pair, each located on either side of an orifice of a valve. Alternatively, the radiopaque member 39 itself can be formed into a distinctive shape, such as a >T=, such that it has a different radiographic profile in one plane as opposed to another, thus identifying a particular orientation. Preferably, such a distinctive shape would need to be sufficiently large to be easily imageable, the size being determined by the type and resolution of the imaging system selected. Various configurations and methods for affixing the radiopaque maker into the aperture are described in U.S. Pat. No. 6,464,720 to Boatman et al., the disclosure of which is expressly incorporated by reference into this application.

FIGS. 7-8 depict alternative methods of adding materials to the support structure 15 to create a radiopaque marker 39 at a particular bend 18. In the illustrative embodiment of FIG. 7, the struts 20,21 (and apex of the bend 43) include a layer 46 of radiopaque material which is applied or deposited in one of any well-known manners appropriate for that particular material, including dipping, electrostatic deposition, spraying, painting, overlaying, wrapping, etc. One example of adding a layer 46 of radiopaque material is to dip the bend 43 in molten gold. Optionally, a protective polymer overcoat may applied as well to prevent flaking and degradation of the thin layer 46 of outer material. Furthermore, a polymer resin coating could be substituted that includes radiopaque filler material such as barium sulfate, bismuth, or tungsten powder. FIG. 8 depicts an alternative embodiment comprising a pair of imageable elements 13,14 made of radiopaque wire 77 or thread (i.e., gold, platinum, titanium, etc.) that is wrapped around the struts 20,21 to form a radiopaque member 39. The radiopaque members of FIGS. 7-8 can be used to mark a single bend or used in combination to define a valve orifice as opposing imageable elements 13,14 at opposite bends.

As an alternative to adding one or more radiopaque members 39 to the support structure 15 for orienting the prosthesis 10, one or components of the support structure 15 itself can be made of radiopaque metal or other material that would permit orientation of the prosthesis under fluoroscopic or x-ray guidance. FIGS. 9-10 depict the support structure 15 of the exemplary venous valve depicted in FIG. 1 comprising a number of components that are interconnected by a series of cannulae 51,52,53,54,55,56,62,63. In an example of using the support structure 15 as imageable structure 12, one of more of the cannulae 51,62 at the first bend 43 and one or more cannulae 55,80 at the second, opposite bend 44 can comprise a radiopaque material to permit orientation of the orifice 24 therebetween. FIG. 10 depicts the embodiment of FIG. 9 in a compressed state 75 whereby the at least two of cannulae 51,55,62 and 63 would be visible, if made sufficiently radiopaque, thereby allowing the radiologist to determine that the orifice 24 was generally perpendicular to his or her plane of view 67 (see FIG. 9), particularly if the prosthesis is rotated such that the radiopaque cannula or cannulae marking at each of the first and second bends 43,44 are the maximum distance apart from one another. If rotated $90_L$ to a second plane of view, any radiopaque cannula 51,55, or 61,63 would be superimposed over one another so that they would appear as a single radiopaque element 39 located midway within the prosthesis 10 and delivery catheter 59. Obviously, two closely-spaced radiopaque markers would indicate that the orifice 24 was oriented somewhere between planes 67 and 68 relative to the viewer. Alternatively, both radiopaque cannulae can be placed at a single bend 18, rather than opposites bends 43,44 (e.g., cannula 51 and cannula 62). Depending on the ability of the imaging system to allow the operator to discern two close, but separate radiopaque markers 39, the plane of the orifice 24 can be determined, For example, when a single visible radiopaque element 39 is visible under imaging, it generally indicates that the orifice 24 is lying in a plane perpendicular to the viewer.

Figure 20:
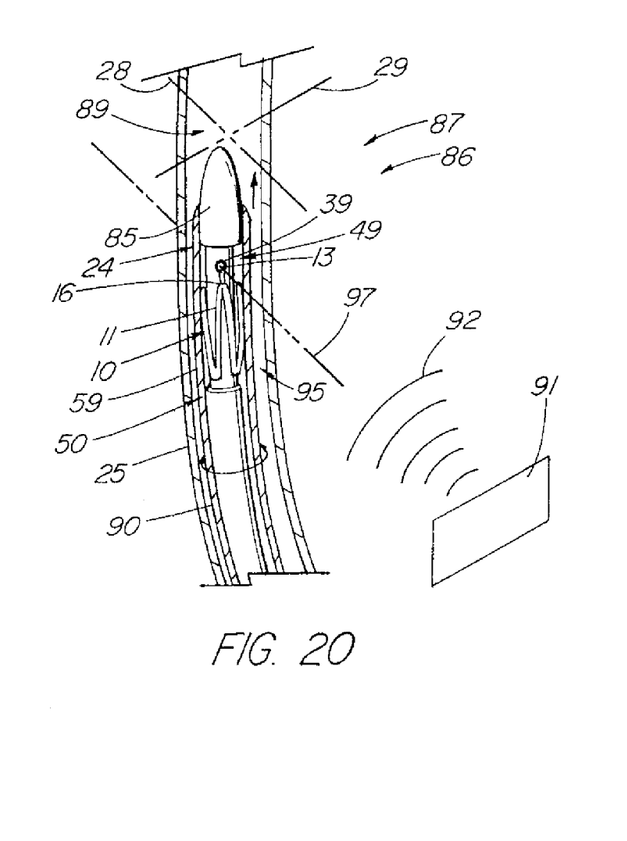
FIG. 20 depicts a partially sectioned view of a valve being placed using a ascending approach.

The basic method for placing a valve 11 in a vessel or vein 25 is depicted in FIG. 20. Using an external imaging unit or system 91, such as the illustrative fluorosope, a radiographic beam 92 allows the clinician to visualize the delivery system 86 on a monitor as it is advanced to the implantation site 95 following its introduction via a venous puncture (not shown) which in the illustrative example, is made into a vein at a site located below the implantation site 95 so that the delivery apparatus 86 is withdrawn distally (toward the feet) after deployment. At the implantation site 95, the clinician determines the location of the imageable marker, which in the figure, comprises a radiopaque marker 39 generally aligned in lateral profile with location of the orifice 24 of the leaf structure 16 (preferably a pair of opposing radiopaque marker 13,14 disposed about opposite ends or bends 43,44 of the orifice as depicted in FIG. 1). The clinician uses the radiopaque marker 39 to longitudinally align the valve 11 at the deployment site, such as using the method described above for FIGS. 7-8. Optionally, he or she may rotationally orient the valve, such as to align the orifice 24 or other structural feature of the prosthesis 10 with a particular anatomical feature of the implantation site 95 (e.g., the long 28 or short 29 axis of the vessel 25). The clinician rotates the delivery system 86 within the vessel 25 to orient the first axis 97 transecting the imageable structure 12 (radiopaque marker(s) 39) and structural feature or orifice 24 of the prosthesis until the imageable structure/structural feature and the desired anatomical feature are generally in alignment within the desired plane that allows confirmation of alignment (typically in alignment with or perpendicular to the plane of view provided by the imaging beam. Preferably, the anatomical feature, such as the illustrative long axis of the vessel 28 is either directly aligned with the plane of view or is perpendicular thereto to facilitate correct placement of the prosthesis and eliminate a potential sources of confusion during the alignment process. The outer constraining member 59 or delivery catheter is withdrawn, deploying the self-expanding valve 11 (which typically comprises a nitinol or stainless steel support structure) such that the valve is anchored at the site 95 and is able to function in manner similar to a competent native venous valve to restrict retrograde flow. The inner member 85 over which the valve was mounted is then withdrawn through the expanded valve and removed via the original venous puncture site.

Again referring to FIGS. 9-10, the cannulae comprising radiopaque markers 39 can be distributed in other ways that would facilitate fluoroscopic orientation of the prosthesis 10. For example, those cannulae located toward the second or distal end 79 of the valve (e.g., cannulae 54 and 58 and/or 53 and 57), if radiopaque, would indicate that the orifice 24 was lying perpendicular to the viewing plane if centered within the prosthesis 10 as it is imaged. These cannulae 53,54,57,58 can be used in combination with selected ones at the first or proximal end of the prosthesis 78 to form a pattern of radiopaque markers 39 that indicate the rotational orientation of the device 10.

As an alternative to making the cannulae radiopaque, other portions of the support structure 12 can comprise radiopaque material, such as the barbs, struts, bends or sections comprising a combination thereof. In the embodiment of FIG. 9, barb struts 22,60 can be made of radiopaque materials such that if the orifice is perpendicular to viewing angle 67, they converge toward the second end 79 of the prosthesis 10. Conversely, if rotated $90_L$ counter-clockwise, barbs 22 and 61 (assuming they are both radiopaque) would also appear as a V-shaped radiographic image, but with the anchoring barb portions 23 converging toward the first or proximal end 78 of the prosthesis 10.

Again referring to FIG. 9, other portions of the frame, such as one of more of the lateral arms or bend 32,33,34,35 of the illustrative prosthesis, can be made of radiopaque material to create a unique profile for identifying the orientation of the device. In the illustrative embodiment, these radiopaque sections 32,33,34,35 would appear W-shaped under fluoroscopy when oriented generally perpendicular to a given viewing angle.

Figure 11:
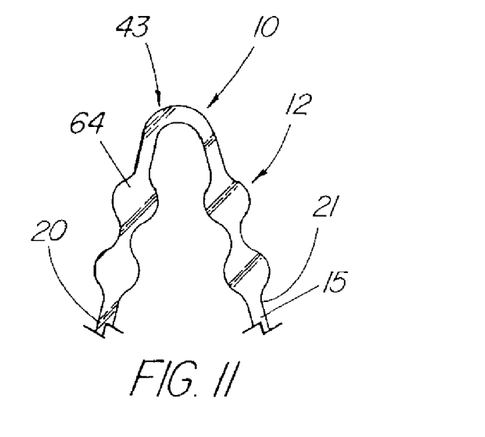
FIGS. 11-12 depict a side view of an embodiment of the present invention in which a portion of the support structure comprises a distinctive radiographic profile.
Figure 12:
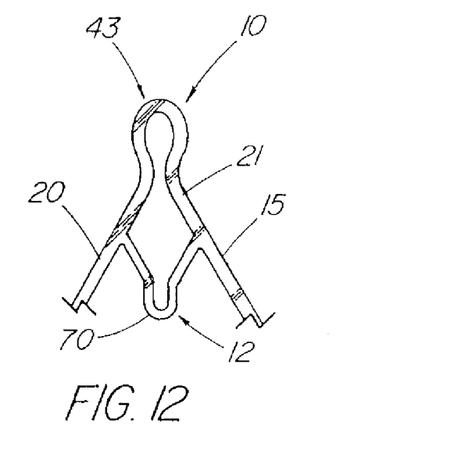

As an alternative to the use of radiopaque elements as markers to indicate orientation of the device, the imageable structure 12 can comprise a support structure 15 in which a portion or region thereof comprises a visually distinctive imageable structure 12, such as particular shapes or additional elements that offer a unique profile under imaging, examples of which are depicted in FIGS. 11-12. As with radiopaque elements or markers, the location of the imageable structure 12 provides a visual identification cue to a structural feature of the device, such as a valve orifice, side opening, anchoring means, etc., the location of which on the prosthesis would need to be known by the clinician. The support structure 12 of the present invention would comprise materials or a configuration that is capable of producing a sufficient radiographic or other type of image that would permit the clinician to discern or recognize the portion of the prosthesis having distinctive imageable structure 12 critical for the identification of the feature of interest.

In the embodiment of FIG. 11, the imageable structure 12 comprises a plurality of enlarged areas 64 along the struts 20,21 that provide a distinct profile under imaging. This allows for the identification of the adjacent interconnecting bend 43 as having significance to the desired orientation of the device 10, such as to mark two opposite bends 43,44 as in the embodiment of FIG. 1. Similarly, imageable structure 12 can be added to the bend 43 by adding a supplemental strut 70, such as depicted in the embodiment of FIG. 12, in which an extra V-shape strut 70 extends from struts 20 and 21 adjacent to bend 43. By restricting such a supplemental strut 18 to any bend or region which could be used to identify the preferred orientation of the prosthesis in the manner previously discussed. The examples in FIGS. 11-12 are merely exemplary and one skilled in the art could readily conceive of other structural adaptations that would provide a distinctive imageable profile, while possibly offering certain structural advantages as well.

Figure 13:
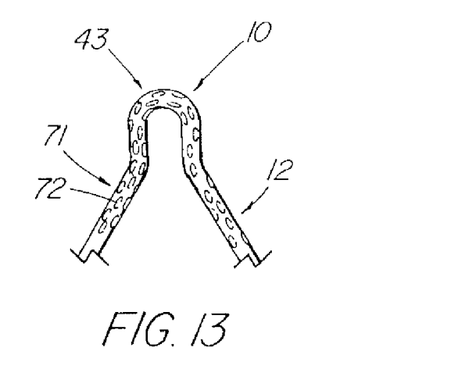
FIG. 13 depicts a side view of an embodiment of the present invention in which the support structure includes an ultrasonically reflective surface.

While intraluminal prostheses are most commonly placed with the aid of fluoroscopy or x-ray, other methods of imaging can prove useful or necessary in some clinical situations. FIG. 13 depicts a bend 43 in which the imageable structure 12 comprises an ultrasonically reflective surface 71 comprising a plurality of indentations 72 of a particular density and configuration for enhancing the imageability of that particular area of the prosthesis. The illustrative ultrasonically reflective surface 71 is described in U.S. Pat. No. 5,081,997 to Bosley, with the disclosure thereof being expressly incorporated by reference into this application. As with the radiographic markers previously discussed, the ultrasonically reflective surfaces 71 can identify key points along the prosthesis that provide the same assistance in allowing the clinician to orient the prosthesis to optimize its function.

Figure 14:
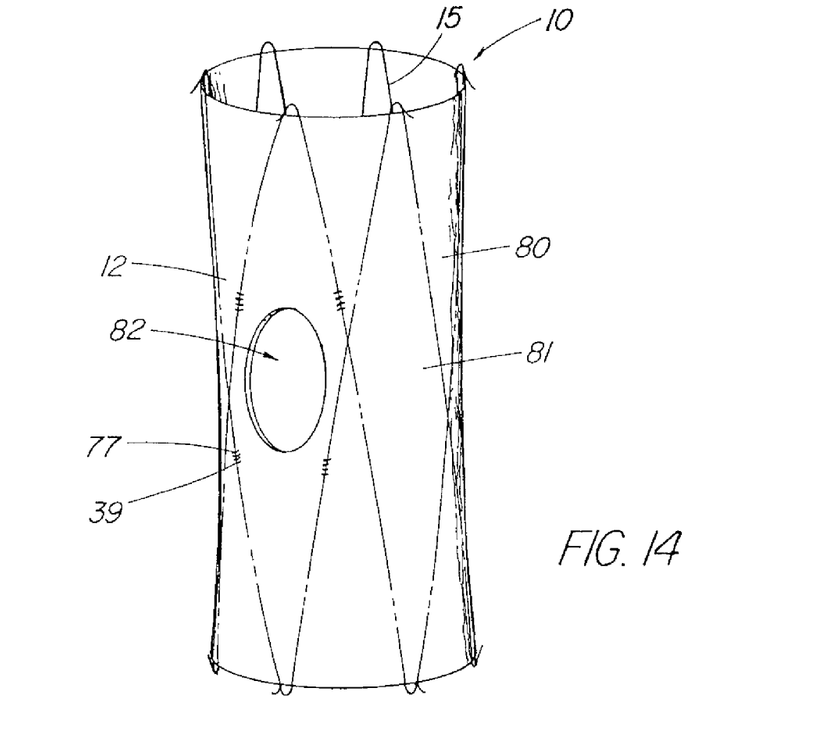
FIGS. 14-15 depict perspective views of covered stent embodiments of the invention which include a side aperture with radiopaque markers
Figure 15:
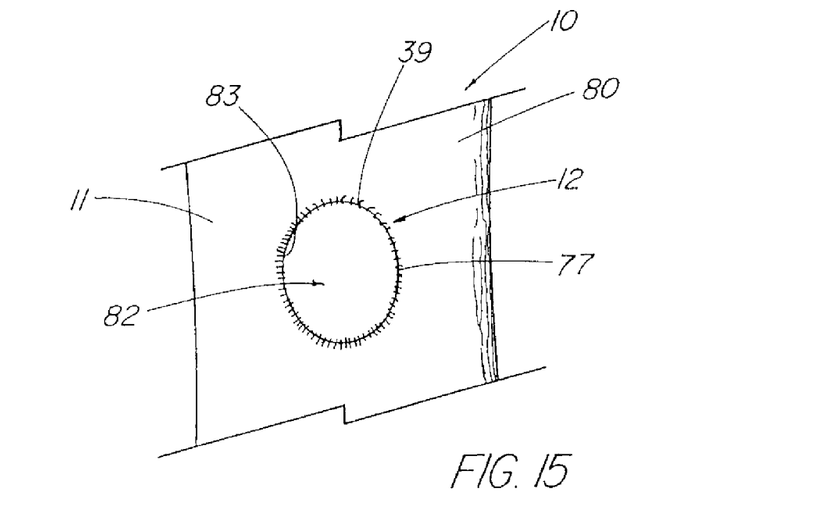

The imageable structure 12 of the present invention can be utilized to identify other structural features of the prosthesis 10 that provide a particular function or clinical advantage. FIG. 14 depicts a covered stent 80 with an aperture 82 in the covering material 81, such as one that would allow alignment with the opening to a branch vessel or duct. The aperture 81 may exist at only one location along the circumference of the stent, or there may be oppositely placed apertures aligned along an axis, such as to accommodate both right and left branch vessels. To permit identification of the aperture under fluoroscopy, the aperture is bordered by a series of radiopaque markers 39, which in the illustrative embodiment, comprise radiopaque wire 77 or thread that is wrapped around the struts of the support structure 15 to form a >box= that surrounds and generally corresponds to the outer border of the aperture 82. The radiopaque wire 77 can either by wrapped around the struts only, or it can be threaded through the material to bind the support structure 15 to the material 81. In another embodiment depicted in FIG. 15, the imageable structure 12 comprises a radiopaque marker 39, such as the illustrative radiopaque thread 77, that rings the edges 83 of the aperture 82 within the covering material 81 of a stent graft 80 of other prosthesis to provide precise identification of the extent of the aperture 82. The radiopaque thread 77 can either be stitched by hand or machine-stitched with a suitable sewing or suturing device. The radiopaque wire or thread 77 depicted in FIGS. 14-15 is merely exemplary of the various types of radiopaque markers 39 and other imageable structure 12 that can be used or configured to identify the aperture 82 or another feature, such as a slit, port, bifurcation, etc.

Figure 24:
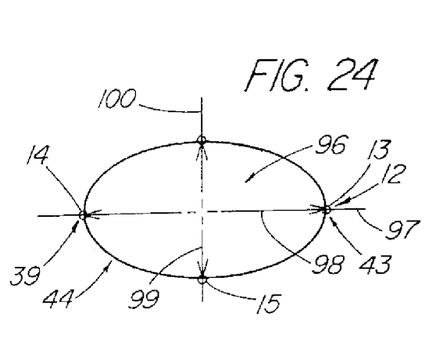
FIG. 24 depicts a top view of a prosthesis of the present invention in which the structural feature comprises a long axis of an elliptical-shaped passageway.

FIG. 24 depicts another embodiment of the present invention in which the structural feature of the prosthesis 10 comprises passageway 86 having a longer first diameter 98 measured along the first axis 97 than a second passageway diameter 99 located about the second axis 100 located perpendicular to the first axis such that the passageway, as viewed from above, is of an elliptical shape, such as to better conform with an elliptically shaped vessel. For example, the support frame 15 of such a prosthesis 10 can be formed of an elliptical shape with prosthesis comprising a valve with an orifice lying along the long first axis 97 such that the structural feature comprises both the first passageway diameter 98 and the orifice (not shown in this example). The imageable structure 12 of the illustrative example comprises a first and second radiopaque marker 13,14 located at the first and second bends 43,44 located along the long passageway diameter 98 and thus, the first axis 97. It is certainly within the scope of this invention that the imageable structure 12 be located about the short passageway diameter 99 such that the short diameter becomes the main structural feature of interest and thus, the first axis 97 is coincident with the shorter passageway diameter 99. A valve orifice, if present, would become a secondary structural feature (such as 101 in FIG. 16) that does not lie on the first axis that includes the imageable structure 12, being disposed instead on a second axis 100 perpendicular to the first axis 97. Referring now to the example of FIG. 16, the second axis 100 optionally may include secondary imageable structure 102, such as radiopaque markers (not shown) at bends 43 and 44, that identifies the secondary structural feature 101 (orifice 24 in this example), although it is preferred that the secondary imageable structure 102 being visually distinguishable from the first imageable structure 12 under external imaging so that the relative orientation of the structural feature (long diameter 98 in FIG. 24, leaflet inner edges 73 in FIG. 16) and the secondary structural feature (the valve orifice 24) can be determined radiographically or by some other appropriate imaging means.

Figure 16:
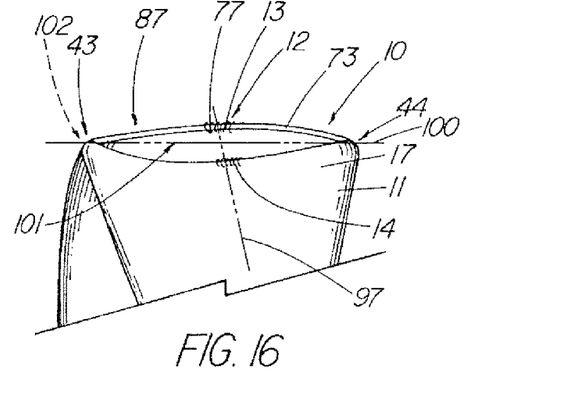
FIG. 16 depicts a perspective view of an embodiment of the present invention in which the leaflets each include a radiopaque marker.
Figure 17:
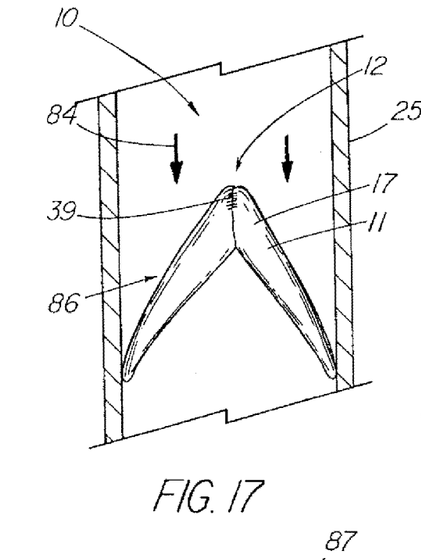
FIGS. 17-18 depict side views of the valve of FIG. 16 in the open and closed position.
Figure 18:
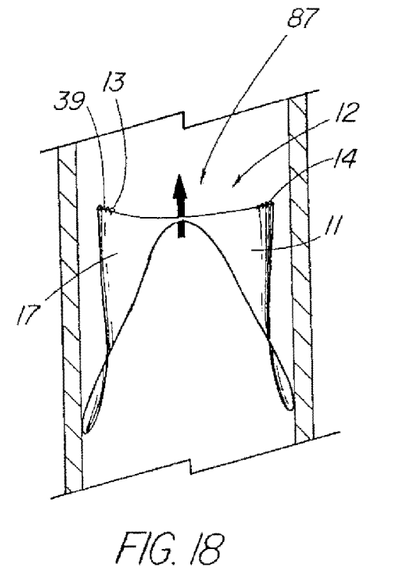

FIGS. 16-18 depict an artificial valve prosthesis 11 of the present invention in which the imageable structure 12, consisting of a pair of radiopaque markers 39, is placed on the leaflets 17 so that under imaging, the clinician can determine if the leaf structure 17 is functioning (coapting) to regulate blood flow and prevent excessive reflux back through the valve. In the embodiment depicted in FIG. 16, a first and a second 13,14 radiopaque element are placed on opposing leaflet 17, by attaching the radiopaque elements 13,14, which comprise radiopaque thread 77 (gold, platinum, etc.) in the illustrative embodiment, about the inner edges 73 of the leaflets 17 (either at or near the leaflet edges) such that the markers 13,14 are able to come in close proximity to one another when the valve 11 is deployed in a vessel 25 and is in the closed or coapted position 86 due to retrograde flow 84 closing the valve, as shown in FIG. 17. As the leaflets 17 move into the open position 87 in response to normal antegrade blood flow 85 toward the heart, the radiopaque elements 13,14 move away from one another. This movement is detectable under fluoroscopic monitoring and would be indicative of a functioning valve 11. Conversely, if one or both leaflets 17 were to adhere to the wall of the vessel 25 or would be immobilized due to thrombus or some other reason, this should be apparent as well. If the radiopaque elements 13,14 do not appear to be meeting one another when viewed under fluoroscopic monitoring, this could be indicative of an incompetent valve 11 that cannot seal sufficiently. The imageable structure 12 shown in FIGS. 16-18 is but one possible embodiment. One skilled in the art would appreciate that there are a wide variety of possible radiopaque elements and materials that can be attached to or adjacent the leaflets 17 or applied thereover to make them at least partially visible under external imaging. Metallic or radiopaque polymer beads or disks can be attached to or through the leaflet service. Redundant leaflets or partial leaflets made of a radiopaque material can be placed in tandem with the primary leaflet 17 so that movement of the primary leaflet can be detected. Radiopaque particulate or fluid materials can be incorporated into or bonded onto the leaflet 17 to enhance radiopacity. The surface of the leaflets can also be made ultrasonigraphically reflective. It also should be noted that the first and second radiopaque elements 13,14 can be used together with radiopaque markers placed on the opposing proximal bends 43,44 or elsewhere so that the orifice 24 can be visualized under imaging as well.

Figure 19:
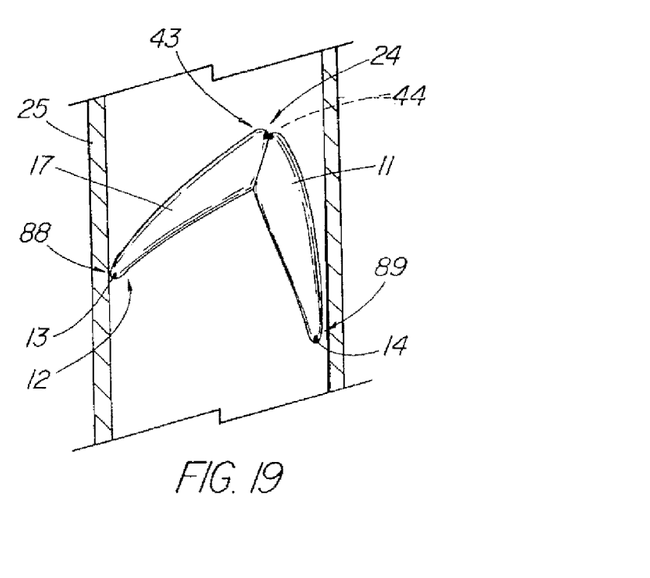
FIG. 19 depicts a side view of an embodiment of the present invention that includes additional radiopaque markers to indicate whether the prosthesis has tilted at or following deployment.

In addition to placing radiopaque markers 39 on a valve prosthesis 11 at the proximal bends 43,44 to define the orifice 24, or about the leaflets 17 as a means of determining their functionality, imageable structure 12, such as the illustrative first and second radiopaque markers 13,14 placed at distal bends 88 and 89, can provide an indicator as to whether the valve 11 has tilted at or following deployment in the vessel 25, as depicted in FIG. 19. If the path of the vessel 25 can be discerned radiographically, such as by the addition of contrast media, misaligned radiopaque elements 13,14 relative to the vessel path, as is the case with those depicted in FIG. 19, would indicate that the valve 11 is not situated correctly in the vessel 25 and thus, function of the leaflets 17 may be compromised.

Figure 21:
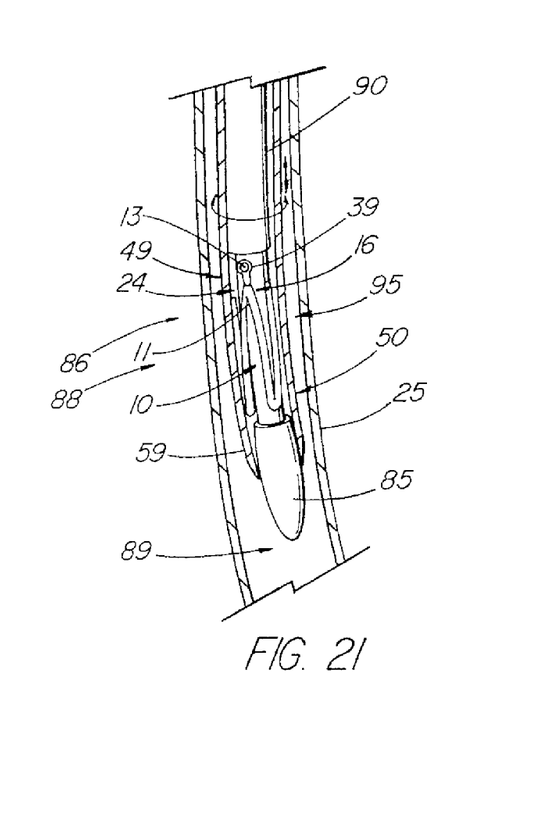
FIG. 21 depicts a partially sectioned view of a valve being placed using an descending approach.

In addition to utilizing the imageable structure to determine the rotational orientation of the structure feature (e.g., valve orifice), the functionality of the structural feature (e.g., leaf structure of a valve), or the longitudinal orientation of the valve (e.g., the presence or absence of tilting), the imageable structure can be useful as an indicator that the prosthesis is oriented within the delivery apparatus such that it will function properly depending on the method of deployment used. FIGS. 20-21 depict the two main methods of approach used to place a venous valve prosthesis at an implantation site 95 within a vein 25, typically one of the deep veins of the lower legs (e.g., poplitea vein). FIG. 20 depicts an apparatus having a first delivery configuration 87 for an ascending approach where a venous puncture (not shown) is made below the implantation site 95 and the delivery apparatus 86 is advanced proximally (toward the heart and head) thereto. In the illustrative example, the valve 11 and orifice 24 are mounted on an inner member 84 and constrained inside a delivery sheath 59 or constraining member (an example of a similar apparatus being more fully disclosed in U.S. Patent Application Publication US2003014467A1 to Pavcnik et al. which is hereby incorporated by reference). The valve 11 is oriented such that the leaf structure 16 at least partially slopes or extends downward away from the orifice 24 toward the second end 50 of the valve such that the leaflets are configured to catch retrograde blood flow, thus causing the leaflets to coapt with one another and seal the valve. In the example of FIG. 20, this results in the valve loaded such that orifice 23, first end of the valve 49, and accompanying radiopaque markers 39 thereabout, are located closest to the distal end 89 of the delivery apparatus 86 so that when deployed using an ascending approach, the valve is oriented in the vessel such that it can function as intended. If the valve is accidently deployed upside down, the leaf structure 16 would likely not permit antegrade flow and thus, occlude the vessel.

FIG. 21 depicts an apparatus in a second delivery configuration 88 for an descending approach for valve placement in which the venous puncture (not shown) is made above the implantation site 95 (such as at the jugular or subclavian vein or groin) and the delivery apparatus 86 advanced downward (toward the feet) thereto. The delivery apparatus 86 and valve 11 arrangement differs from that of FIG. 20 in that the orifice 24, first end 49 of the valve, and radiopaque marker 39 are oriented oppositely, away from the distal end 89 of the delivery apparatus 86, the second end of the valve 49 now lying closest to the distal end 89 instead. This ensures correct deployment of the valve when the descending approach is used. Preferably, some type of indicia 90 (markings, instructions, etc.) will be included on the delivery apparatus 86 (as depicted), the valve prosthesis, or associated packaging material (e.g., outer/inner package, labeling, instructional material insert, etc.) that clearly identifies whether the valve 11 is loaded for an ascending or descending approach with the imageable structure 12 (radiopaque markers 39) providing secondary confirmation that the valve 11 is oriented for the delivery approach that is intended.

Figure 23:
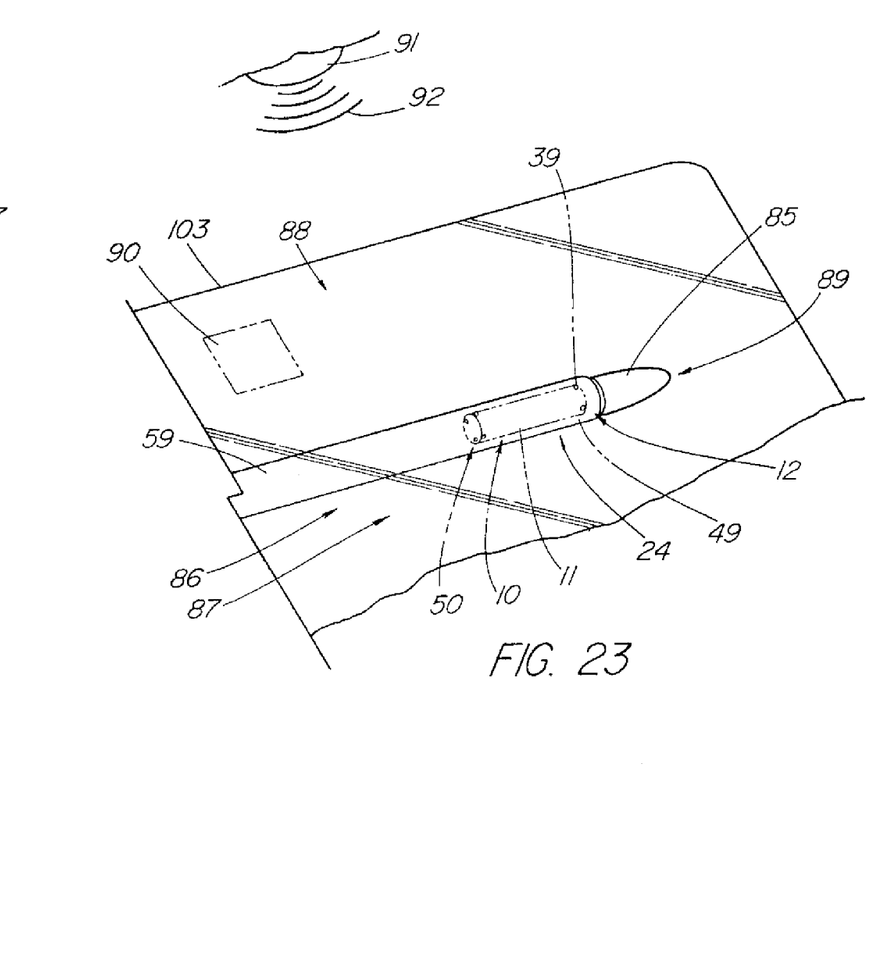
FIG. 23 depicts a method of determining the orientation of the valve prior to use within an patient.

FIG. 23 depicts a method of ascertaining or confirming whether a valve 11 preloaded inside a delivery apparatus 86 is in the first or second configuration 87,88 delivery via an ascending or a descending approach, respectively. In the illustrative example, the valve 11 is oriented inside the delivery apparatus 86 in the ascending approach configuration 87. An external imaging system 91, such as a fluoroscopy, x-ray, ultrasound, or M.R.I. machine, etc., emits a beam of energy 92 of the appropriate type so that an operator can view an image of the prosthesis 10 (valve 11) loaded inside the delivery catheter to determine the orientation of the imageable structure 12 (radiopaque marker 39) which is located about the first end 49 and therefore, in this example, should be located closest to the distal end 89 of the delivery apparatus 86. These steps can be performed as a quality control step by the manufacturer before or after packaging, sterilization, or shipping to ensure that the apparatus configuration 87 is consistent with indicia 90 (permanent or temporary) placed on or to be place on the packaging material 103 indicating that the prosthesis is to be placed using the delivery approach (ascending) consistent with that particular delivery configuration 87, or these steps can be performed in a clinical setting prior to introduction of the apparatus (valve 11 and delivery system 86) into the patient by a clinician. For example, even if indicia 90 clearly identify the proper delivery configuration 87,88, packaging material may have been removed at some point and thus, confirmation via external imaging may provide additional assurance to the clinician that the valve is properly oriented for the approach selected. Another potentially problematic situation is when the decision on which approach to use changes, leading to potential confusion in associating the right apparatus with the right procedure. To help eliminate such confusion, it is preferable to include clear markings or labeling located on the delivery apparatus 86 itself to indicate the orientation of the valve and the proper direction or approach to be used with that particular delivery configuration.

Figure 22:
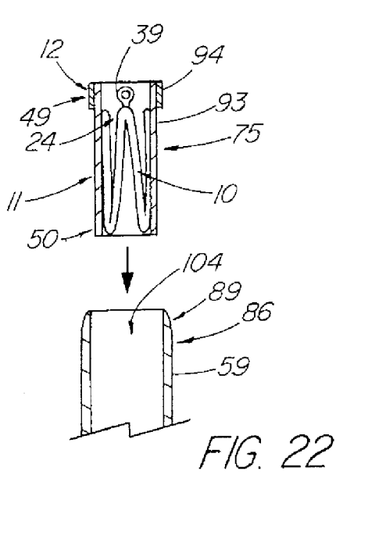
FIG. 22 depicts a partially sectioned view of a valve in a loading cartridge for insertion into a delivery apparatus.

FIG. 22 depicts a valve prosthesis 10 that further comprises a loading element 93, such as constraining cartridge that is sized and configured for insertion into the passageway 104 of the constraining member 59 or catheter of the delivery apparatus 86. The loading process can be done just prior to the delivery process, thus allowing the same delivery apparatus to be used, regardless of whether a ascending or descending approach is to be employed. The imageable structure may be located on the valve 11, the loading element 93 or both to identify the location of the structural feature (orifice 24). The illustrative cartridge 93 a radiopaque band 94 that is generally aligned longitudinally with the radiopaque marker 39 located on the valve itself. The loading element may also comprise non-imageable indicia or structure to distinguish the different ends 49,50 of the valve within and to identify the proper orientation of the orifice 24.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman=s Medical Dictionary, 27$^{th}$ edition.

What is claimed is:

1. An expandable prosthesis placeable into a body lumen, the expandable prosthesis comprising:
    a support structure configured to engage the walls of the body lumen, the support structure having a cross-sectional profile that includes a first axis;
    an artificial valve attached to the support structure and comprising a pair of opposing leaflets that define an orifice, the orifice including a first end and a second end located about the first axis; and
    a first radiopaque member located about the first end of the orifice and a second radiopaque member located about the second end of the orifice, each of the first radiopaque member and the second radiopaque member configured to facilitate visual identification of the rotational orientation of the first axis and the orifice while the prosthesis is being imaged externally;
    wherein the orifice of the artificial valve opens and closes in response to fluid flowing therethrough.

2. The expandable prosthesis of claim 1, wherein the support structure includes a first aperture and a second aperture;
    wherein each of the first radiopaque member and the second radiopaque member comprises a central portion and two terminal portions, the central portion of the first radiopaque member traversing the first aperture with the two terminal portions of the first radiopaque member each having a diameter greater than the first aperture, the central portion of the second radiopaque member traversing the second aperture with the two terminal portions of the second radiopaque member each having a diameter greater than the second aperture.

* * * * *